US007390837B2

(12) United States Patent
Zhu et al.

(10) Patent No.: US 7,390,837 B2
(45) Date of Patent: *Jun. 24, 2008

(54) GERMICIDAL COMPOSITIONS CONTAINING PHENYLMALONALDEHYDE-TYPE COMPOUNDS, OR MIXTURES OF PHENYLMALONALDEHYDE-TYPE COMPOUNDS AND PHTHALALDEHYDES, AND METHODS OF USING SUCH COMPOSITIONS FOR DISINFECTION OR STERILIZATION

(75) Inventors: Peter C. Zhu, Irvine, CA (US); Charles G. Roberts, Long Beach, CA (US)

(73) Assignee: Ethicon, Inc., Somerville, NJ (US)

(*) Notice: Subject to any disclaimer, the term of this patent is extended or adjusted under 35 U.S.C. 154(b) by 145 days.

This patent is subject to a terminal disclaimer.

(21) Appl. No.: 10/769,598

(22) Filed: Jan. 30, 2004

(65) Prior Publication Data

US 2005/0171121 A1 Aug. 4, 2005

(51) Int. Cl.
*A01N 35/00* (2006.01)
*A61K 31/11* (2006.01)

(52) U.S. Cl. ......................... 514/693; 514/699; 514/705

(58) Field of Classification Search ................ 424/76.8; 514/693, 699, 705
See application file for complete search history.

(56) References Cited

U.S. PATENT DOCUMENTS 1,901,704 A 3/1933 Delles
3,016,328 A 1/1962 Pepper et al.
3,102,811 A 9/1963 Barney
3,229,851 A 1/1966 Horwitt et al.
3,474,176 A 10/1969 Freeman
3,912,450 A 10/1975 Boucher
3,929,662 A 12/1975 Boucher et al.
3,968,248 A 7/1976 Boucher
3,968,250 A 7/1976 Boucher
4,418,055 A 11/1983 Andersen et al.
4,419,368 A 12/1983 Jones et al.
4,436,754 A 3/1984 Jacobs
4,592,892 A 6/1986 Ueno et al.
4,690,772 A 9/1987 Tell et al.
4,698,312 A 10/1987 Wong et al.
4,831,449 A 5/1989 Kimura
4,847,304 A 7/1989 Bruckner et al.
4,851,449 A 7/1989 Bruckner et al.
4,939,203 A 7/1990 Marrocco
4,971,999 A 11/1990 Bruckner et al.
5,107,032 A 4/1992 Erb et al.
5,128,051 A 7/1992 Theis et al.
5,192,459 A 3/1993 Tell et al.
5,250,160 A 10/1993 Oksman et al.
5,338,532 A 8/1994 Tomalia et al.
5,389,685 A 2/1995 Smith et al.
5,424,323 A 6/1995 Wachman et al.
5,429,797 A 7/1995 Camiener
D363,019 S 10/1995 Arnold et al.
5,494,637 A 2/1996 Barlow
5,540,326 A 7/1996 Arnold et al.
5,558,841 A 9/1996 Nakagawa et al.
5,567,385 A 10/1996 Miller et al.
5,662,941 A 9/1997 Bourbon et al.
5,700,377 A 12/1997 Cox
5,761,069 A 6/1998 Weber et al.
5,800,838 A 9/1998 Bourbon et al.
5,863,547 A 1/1999 Miner
5,866,723 A 2/1999 Hamper et al.
5,874,637 A 2/1999 Giselbrecht et al.
5,936,001 A 8/1999 Block
5,945,451 A 8/1999 Kraatz et al.
6,071,972 A 6/2000 Block
6,080,789 A 6/2000 Lutz
6,096,698 A 8/2000 Milling
6,270,784 B1 8/2001 Mrusek et al.
6,297,285 B1 10/2001 Lutz (Continued)

FOREIGN PATENT DOCUMENTS

EP 0292300 11/1988

(Continued)

OTHER PUBLICATIONS

Klimko et al. ("Functional Derivatives of malodialdehydes and their reactions. X. Acetals of malondialdehyde homologs" Zhurnal Obshchei Khimii, 1959, 29, pp. 4027-4029).*

(Continued)

*Primary Examiner*—Sreeni Padmanabhan
*Assistant Examiner*—Yong S. Chong
(74) *Attorney, Agent, or Firm*—Kirkpatrick, Lockhart Preston Gates Ellis LLP

(57) ABSTRACT

Germicidal compositions containing phenylmalonaldehyde-type compounds, or mixtures of phenylmalonaldehyde-type compounds and phthalaldehydes, and methods of using such compositions for killing bacteria, disinfection, or sterilization, are disclosed. In one aspect, a germicidal composition may include a diluent, and a germicidal compound having the formula:

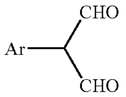

wherein Ar is an aryl group that is selected from the group consisting of phenyl, 4-pyrimidinyl, and 2-(2-nitro-3-formylphenyl). In a further aspect, the composition may also include a germicidal efficacy enhancer such as isophthalaldehyde or a combination of isophthalaldehyde and terephthalaldehyde.

15 Claims, No Drawings

U.S. PATENT DOCUMENTS

| | | | | |
|---|---|---|---|---|
| 6,309,658 | B1 | 10/2001 | Xia et al. | |
| 6,429,220 | B1 * | 8/2002 | Yagi et al. | 514/372 |
| 6,458,554 | B1 | 10/2002 | Hui et al. | |
| 6,461,997 | B1 | 10/2002 | Hegde et al. | |
| 6,552,203 | B2 | 4/2003 | Bertenshaw et al. | |
| 2001/0053333 | A1 | 12/2001 | Messier et al. | |
| 2004/0071653 | A1 * | 4/2004 | Bratescu et al. | 424/70.24 |

FOREIGN PATENT DOCUMENTS

| | | | |
|---|---|---|---|
| EP | 0292301 | | 11/1988 |
| EP | 0552853 | | 7/1993 |
| JP | 09/124538 | | 5/1997 |
| JP | 09124538 | | 5/1997 |
| JP | 11-140010 | | 11/1997 |
| JP | 11140040 | | 5/1999 |
| RU | 2020964 | C1 | 10/1994 |
| SU | 1395329 | A | 5/1988 |
| WO | WO 95/16023 | | 6/1995 |
| WO | WO 00/24761 | | 5/2000 |
| WO | WO-0024761 | | 5/2000 |

OTHER PUBLICATIONS

Duran-Patron et al. ("Structure-Activity Relationships of New Phytotoxic Metabolites with the Botryane Skeleton from Botrytis cinerea" Tetrahedron, 55, 1999, pp. 2389-2400).*

Cidex® OPA, High Level Disinfection Solution, Technical Info. Advanced Sterilization Products® , © 2004. pp. 1-4.

Cidex® OPA Solution, And Speed Has Its Advantages! © ASP© 2001, 1 pg.

Cidex® OPA Solution Retrieved on Aug. 7, 2003; Retrieved online at : http://www.cidex.com/products_&_services/cidex/cidex_opa/index.asp. pp. 1-2.

E.G.M. Power & A.D. Russell; "Sporicidal action of alkaline glutaraldehyde: factors influencing activity and a comparison with other aldehydes"; Journal of Applied Bacteriology 1990,69, pp. 261-268.

Jose-Luis Sagripanti and Aylin Bonifacino; Food Biological Contaminants; "Effects of Salt and Serum on the Sporicidal Activity of Liquid Disinfectants"; Journal of AQAC International, vol. 80, No. 6, 1997; pp. 1198-1207.

Hiroshi Kuronuma, Journal of Japanese Society of Hospital Pharmacists, vol. 36, No. 1, 2000. In Japanese; translation of introduction. "Stability of Ortho-Phthalaldehyde Solutions under Various Storage Conditions". pp. 55-58.

B. Setlow, et al.; "Mechanisms of killing spores of Bacillus subtilis by acid, alkai and ethanol"; Journal of Applied Microbiology 2002, 92, pp. 362-375.

Anthony C. H. Durham; "A Survey of Readily Available Chelators for Buffering Clacium ION Concentrations in Physiological Solutions", Cell Calcium 4: pp. 33-46, 1983.

S.D. Rubbo, et al.; (Symposium of Chemical Disinfection: Paper VIII); "Biocidal Activities of Glutaraldehyde and Related Compounds", 1967, J. Appl. Bact. 30(1) pp. 78-.

Mislow et al., Optical Resolution of 1, 2, 5, 6-Dibenzocyclooctateraene derivative. Journal of the American Chemical Society, vol. 84, 1962 p. 3591-3592. Aug. 3, 1962.

Preparation of aromatic polyaldehydes by hydrolysis of gem-dibromides. Li, Mingwei; Fan, Nengting. Beijing No. 1 Light Ind. Inst., Beijing, Peop. Rep. China. Huaxue Shijie (1985), 26(5), 168-70. Journal written in Chinese. Abstract Translated.

*Symposium of Chemical Disinfection: Paper VIII, J. Appl. Bact. 30(1)*, (1967), 78-87.

Sagripanti, Jose-Luis, "Effects of Salt and Serum on the Spricidal Activity of Liquid Disinfectants", *Journal of AQAC International, vol. 80, No. 6*, (1997), 1198-1207.

Setlow, B. , "Mechanisms of Killing Spores of Bacillus Subtillis by Acid, Alkali and Ethanol", *Journal of Applied Microbiology (92)*, (2002),362-375.

Advanced Sterilization Products, "Cidex® OPA Solution, And Speed Has Its Advantages", (2001),1.

Advanced Sterilization Products, "Cidex® OPA Solution", http://www.cidex.com/products_&_services/cidex/cidex_opa/index/asp. retrieved Aug. 7, 2003,(2003),1-2.

Advanced Sterilization Products, "Cidex® OPA, High Level Disinfecting Solution", *Technical Info.*, (2004),1-4.

Durham, Anthony C., "A Survey of Readily Available Chelators for Buffering Calcium Ion Concentrations in Physiological Solutions", *Cell Calcium 4*, (1983),33-46.

Kuronuma, Hiroshi , "Srability of Ortho-Phthalaldehyde Solutions Under Various Storage Conditions", *Journal of Japanese Society of Hospital Pharmacists*, vol. 36, No. 1, (2000),55-58.

Li, Mingwei , et al., "Preparation of Aromatic Polyaldehydes by Hydrosis of Gem-Dibromides", *Beijing No. 1 Light Ind. Indst., Beijing, Peoples Republic of China Huaxue Chiejie*, 26(5). Journal written in Chinese (Abstract Translated),(1985),168-170.

Mislow, Kurt , et al., "Optical Resolution of a 1, 2, 5, 6-Dibenzcyclooctatetraene Derivative", *Journal of the American Chemical Society*, vol. 84, (Aug. 3, 1962),3591-3592.

Power, E.G.M. , "Spricidal Action of Alkaline Glutaraldehyde: Factors Influencing Activity and a Comparison With Other Aldehydes", *Journal of Applied Bacteriology*, (1990),261-268.

Rehn, D. , et al., "About the Antimicrobial Activity of Substituted Aromatic Aldehydes", *Zbl. Bakt. Hyg: I. Abt. Orig.*, vol. B172, tables 1, 2, XP002325401,(1981),508-519.

Rubbo, S.D. , "Biocidal Activities of Glutaraldehyde and Related Compounds".

* cited by examiner

GERMICIDAL COMPOSITIONS CONTAINING PHENYLMALONALDEHYDE-TYPE COMPOUNDS, OR MIXTURES OF PHENYLMALONALDEHYDE-TYPE COMPOUNDS AND PHTHALALDEHYDES, AND METHODS OF USING SUCH COMPOSITIONS FOR DISINFECTION OR STERILIZATION

BACKGROUND

1. Field

An embodiment of the invention relates to a germicidal composition and method of using the composition for disinfection or sterilization.

2. Background Information

Various germicidal compounds, compositions containing the germicidal compounds, methods of using the compounds or compositions for disinfection or sterilization have been discussed in the literature.

Among the germicidal compounds are aldehyde or dialdehyde compounds, such as formaldehyde, glutaraldehyde, or o-phthalaldehyde (also known simply as phthalaldehyde or OPA). Formaldehyde and glutaraldehyde have undesired properties. Formaldehyde is potentially carcinogenic and has an objectionable odor. Glutaraldehyde likewise has an objectionable odor, and may be chemically unstable during storage. Phthalaldehyde has certain advantages over formaldehyde and glutaraldehyde. Phthalaldehyde is generally not regarded to be carcinogenic, and is substantially odorless. However, phthalaldehyde may stain certain surfaces black. Surfaces that may be stained include skin, hair, some clothing, some gloves, and some environmental surfaces. Phthalaldehyde may also stain protein on improperly cleaned medical instruments. In some cases, the staining is indelible and difficult to remove. Although this staining may potentially help to indicate improper cleaning, some practitioners find this staining property objectionable. Phthalaldehyde also has limited solubility in water and costly miscible solvents have been employed to increase the water solubility. Another potential problem with these, and other known germicidal compounds, is that microorganisms may adapt to the compounds and become resistant to their germicidal properties. Accordingly, the germicidal efficacy of these compounds may decrease over time.

Accordingly, there is a general need in the art for new germicidal compounds for disinfection or sterilization. In one aspect, there is a need for germicidal compounds with reduced staining properties. In another aspect, there is a need for germicidal compounds with increased solubility in water.

DETAILED DESCRIPTION

In the following description, numerous specific details are set forth. However, it is understood that embodiments of the invention may be practiced without these specific details. In other instances, well-known structures and techniques have not been shown in detail in order not to obscure the understanding of this description.

I. Germicidal 4-Halo-Phthalaldehydes

The inventors have discovered novel germicidal compositions containing 4-halo-phthalaldehyde compounds, and methods of using the 4-halo-phthalaldehyde compounds for disinfection or sterilization. An embodiment of the invention comprises a composition or method of sterilization involving a 4-halo-phthalaldehyde germicidal compound having the generalized formula (I):

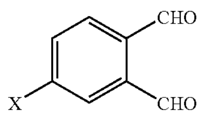

(I)

where X is a halogen, such as fluorine, chlorine, bromine, or iodine. When X is fluorine the compound is 4-fluoro-phthalaldehyde (also known as 4-fluoro-1,2-benzenedicarboxaldehyde; [89226-83-5]); when X is chlorine the compound is 4-chloro-phthalaldehyde (also known as 4-chloro-1,2-benzenedicarboxaldehyde; [13209-31-9]); when X is bromine the compound is 4-bromo-phthalaldehyde (also known as 4-bromo-1,2-benzenedicarboxaldehyde; [13209-32-0]); etc. Other embodiments of the invention include methods of making the 4-halo-phthalaldehyde compounds (see Section VIII).

The 4-halo-phthalaldehyde compounds have germicidal activity and may be used for disinfection or sterilization. Typically, the compounds will be used to form germicidal compositions including the compound as an active ingredient and a diluent. As is known a diluent is a diluting agent that may be used to thin or reduce the concentration of another component by combining or mixing in the diluent with the other component. A diluent may include one or more solvents. Suitable diluents include, but are not limited to, water, aqueous solutions, alcohols (for example methanol, ethanol, isopropanol, butanol, etc.), polyols (for example ethylene glycol or its oligomers or polymers, propylene glycol or its oligomers or polymers, glycerol, etc.), other organic solvents (for example tetrahydrofuran, dimethylsulfoxide, dimethylformamide, acetone, dioxane, etc.), and combinations of such diluents. Aqueous solutions are often appropriate and cost effective and may include other components, such as pH-adjusters, buffer salts, chelating agents, corrosion inhibitors, surfactants, alcohols, or other miscible solvents, fragrances, coloring agents, and the like.

In Examples 1 to 3, which follow, several germicidal solutions containing either the 4-fluoro-, 4-chloro-, or 4-bromo-phthalaldehyde compound were tested to determine their effectiveness in killing at least $1\times10^6$/mL of *Mycobacterium terrae* bacteria using a bacterial suspension test. The bacterial suspension test that was employed is described in Section VII.

The solutions were prepared by adding the appropriate amounts of the germicidal compounds to an aqueous solution. Unless otherwise mentioned all concentrations reported herein are expressed in (w/v) %. The pH of the solution was not adjusted. The tests were conducted at a temperature of about 20° C. (room temperature). The results are presented in terms of log reductions/mL. It is understood that these examples, as well as the other examples herein, are to be construed as merely illustrative, and not limiting.

EXAMPLE 1

Germicidal solutions containing 0.25% of 4-fluoro-phthalaldehyde were tested at exposure times of 30 and 60 minutes. The results are shown in Table 1.

TABLE 1

| Exposure Time (minutes) | Log Reductions/mL (0.25%, 20° C.) |
|---|---|
| 30 | 5.6 |
| 60 | Total Kill |

The results show that, under the test conditions, about 0.25% of 4-fluoro-phthalaldehyde is effective to achieve a total kill of the bacteria in from 30 to 60 minutes at a temperature of 20° C.

EXAMPLE 2

Germicidal solutions containing either 0.2 or 2.7% of 4-chloro-phthalaldehyde were tested at an exposure time of five minutes. The 2.7% solution included 20% isopropanol to increase solubility. The results are shown in Table 2.

TABLE 2

| Compound Concentration (w/v %) | Log Reductions/mL (20° C., 5 min) |
|---|---|
| 0.2 | 5.9 |
| 2.7 (in 20% isopropranol) | Total Kill |

The results show that, under the test conditions, a concentration between about 0.2 to 2.7% of the 4-chloro-phthalaldehyde is effective to achieve a total kill of all bacteria in just five minutes at a temperature of 20° C. Based on the high log reduction of the 0.2% solution, it may be possible to achieve a total kill with less than 1% of the compound. In a separate experiment, a 20% isopropanol solution containing no chlorinated compound was found to be confluent to the bacteria (more than too many bacteria remaining to count) in five minutes at 20° C., indicating that the isopropanol had no significant effect on the log reductions.

EXAMPLE 3

Germicidal solutions containing 0.1% of 4-bromo-phthalaldehyde were tested at exposure times of 10 and 30 minutes. The results are shown in Table 3.

TABLE 3

| Exposure Time (minutes) | Log Reductions/mL (0.1%, 20° C.) |
|---|---|
| 10 | 5.6 |
| 30 | Total Kill |

The results show that, under the test conditions, about 0.1% of 4-bromo-phthalaldehyde is effective to achieve a total kill of the bacteria in from 10 to 30 minutes at a temperature of 20° C.

In one aspect, a germicidal composition may include a germicidally effective amount of a 4-halo-phthalaldehyde compound in an aqueous solution or other suitable diluent. The amount may be effective to kill at least $1\times10^6$ *Mycobacterium terrae* bacteria in contact with the composition in less than one hour, less than 30 minutes, or in less than 5 minutes, with a bacterial suspension test at a temperature of 20° C. As demonstrated in Example 1, a composition including about 0.25% of 4-fluoro-phthalaldehyde is effective to achieve a total kill of the bacteria in from 30 to 60 minutes at a temperature of 20° C. As shown in Example 2, a composition including from about 0.2 to 2.7%, or by estimation less than 1%, of 4-chloro-phthalaldehyde, is effective to achieve a total kill of all bacteria in just 5 minutes at a temperature of 20° C. Finally, as demonstrated in Example 3, a composition including about 0.1% of 4-bromo-phthalaldehyde is effective to achieve a total kill of the bacteria in from 10 to 30 minutes at a temperature of 20° C.

In another aspect, the composition at an in-use germicidally effective concentration, depending on exposure time and temperature, may include from 0.05 to more than 2%, or 0.1 to 1% of the germicidal compound. Higher concentrations may be used for shipping the composition to the point of use, and then composition may be diluted to the desired use concentration. A water miscible co-solvent, such as methanol, ethanol, isopropanol, glycols, tetrahydrofuran, dimethylsulfoxide, or dioxane, among others, may be used to increase the solubility of the compound, if desired.

The composition containing the germicidally effective amount of the halogenated compound may be used for disinfection or sterilization. A method according to one embodiment may include disinfecting a surface by contacting the surface with the composition for a period of time and at a temperature effective to achieve disinfection or sterilization of the surface. The surface may be contacted with the composition by immersion, spraying, or coating, for example.

The inventors have discovered that the novel 4-halo-phthalaldehydes also have the unexpected and superior property that they stain substantially less than phthalaldehyde, or are substantially non-staining. As is known in the arts, phthalaldehyde may tend to stain certain surfaces. Surfaces that may be stained include skin, hair, some clothing, some gloves and some environmental surfaces. Phthalaldehyde may also stain protein on improperly cleaned medical instruments. In some cases, the staining is indelible and difficult to remove. Some practitioners find this staining property undesirable. Staining experiments indicate that each of the 4-halo-phthalaldehydes stain less than phthalaldehyde when employed at the same concentrations. The reduced staining characteristics of the halogenated compounds, compared to phthalaldehyde, are unexpected and significant, and may appeal particularly to those practitioners who find the staining property of phthalaldehyde objectionable.

A potential problem with known germicides that are already being used in commerce is that microorganisms may become resistant to the germicides. Microorganisms, such as tuberculosis, which were once relatively easy to kill, may become more resistant to the germicides, and correspondingly more difficult to kill. Certain bacteria are already becoming resistant to glutaraldehyde. New germicides with even small structural differences from known or currently employed germicides may counteract or compromise the microorganisms resistance or tolerance. As such, the new germicides disclosed herein may greatly advance the arts of disinfection and sterilization.

II. Germicidal Propanedials

The inventors have discovered that a number of propanedial compounds have germicidal efficacy. An embodiment of the invention comprises a germicidal composition including a diluent and a germicidally effective amount of a propanedial compound having the formula:

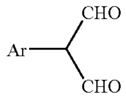

(II)

wherein Ar is an aryl group. Specific compounds investigated by the inventors are listed in Table 4.

TABLE 4

| Compound | Name |
|---|---|
| 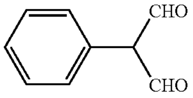 | phenyl-propanedial |
| 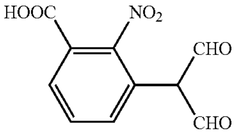 | 3-(1-formyl-2-oxoethyl)-2-nitro-benzoic acid |
| 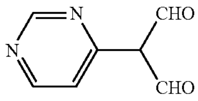 | 4-pyrimidinyl-propanedial |

When Ar is phenyl the compound is phenyl-propanedial (also known as 2-phenyl-1,3-propanedial; [26591-66-2]); when Ar is 4-pyrimidinyl the compound is 4-pyridinyl-propanedial (also known as 2-(4-pyridyl)propane-1,3-dione; [51076-46-1]); when Ar is 2-(3-carboxy-2-nitro)phenyl the compound is 3-(1-formyl-2-oxoethyl)-2-nitro-benzoic acid [205680-83-7]. The compounds are commercially available from Matrix Scientific, of Columbia, S.C. At least 3-(1-formyl-2-oxoethyl)-2-nitro-benzoic acid and 4-pyrimidinyl-propanedial are also commercially available from Acros Organics of Loughborough, Leicestershire, United Kingdom.

The inventors have discovered that the propanedial compounds have germicidal activity and may be used for the novel purpose of disinfection or sterilization. Typically, the compounds will be used to form germicidal compositions including the compound as an active ingredient and a diluent. Suitable diluents include, but are not limited to, water, aqueous solutions, alcohols (for example methanol, ethanol, isopropanol, butanol, etc.), polyols (for example ethylene glycol or its oligomers or polymers, propylene glycol or its oligomers or polymers, glycerol, etc.), other organic solvents (for example tetrahydrofuran, dimethylsulfoxide, dimethylformamide, acetone, dioxane, etc.), and combinations of such diluents. Aqueous solutions are often appropriate and may include other components, such as pH-adjusters, buffer salts, chelating agents, corrosion inhibitors, surfactants, alcohols, or other miscible solvents, fragrances, coloring agents, and the like.

In Examples 4 to 5, which follow, several germicidal solutions containing one of the propanedial compounds were tested to determine their effectiveness in killing at least $1\times10^6$/mL of *Mycobacterium terrae* bacteria using the bacterial suspension test discussed in Section VII. The solutions were prepared by adding the appropriate amounts of the germicidal compounds to an aqueous solution. The pH of the solution was not adjusted. The tests were conducted at a temperature of about 20° C. (room temperature).

EXAMPLE 4

A series of germicidal solutions containing from 0.2% to 1% phenyl-propanedial were tested at exposure times ranging from 5 to 60 minutes. The results are shown in Table 5.

TABLE 5

| Concentration | Log Reductions/mL (20° C.) | | | | |
|---|---|---|---|---|---|
| (%) | 5 min | 10 min | 15 min | 30 min | 60 min |
| 0.2 | Not Tested | Not Tested | Not Tested | Not Tested | 2.1 |
| 0.3 | Not Tested | Not Tested | Not Tested | 2.1 | 3.7 |
| 0.4 | Not Tested | Not Tested | Not Tested | 2.5 | Total Kill |
| 0.7 | Not Tested | 2.5 | Total Kill | Not Tested | Not Tested |
| (~1%) | 4.5 | Not Tested | Not Tested | Not Tested | Not Tested |

The results show that, under the test conditions, from about 0.3 to 0.4% phenyl-propanedial is effective to achieve a total kill of the bacteria within 60 minutes at a temperature of 20° C. From about 0.4 to 0.7% phenyl-propanedial is effective to achieve a total kill within 15 minutes at the same temperature. A 1% solution is able to kill more than 4 logs in just 5 minutes.

EXAMPLE 5

Germicidal solutions saturated with either 4-pyridinyl-propanedial or 3-(1-formyl-2-oxoethyl)-2-nitro-benzoic acid were tested at an exposure time of five minutes. The results are shown in Table 6.

TABLE 6

| Germicidal Compound | Concentration (w/v %) | Log Reductions/mL (5 min, 20° C.) |
|---|---|---|
| 4-pyridinyl-propanedial | Saturated (~2.3%) | 4.0 |
| 3-(1-formyl-2-oxoethyl)-2-nitro-benzoic acid | Saturated (~2.1%) | 4.0 |

The results show that, under the test conditions, about 2.3% 4-pyridinyl-propanedial or about 2.1% 3-(1-formyl-2-oxoethyl)-2-nitro-benzoic acid is effective to kill at least $1\times10^4$ bacteria of *Mycobacterium terrae* in contact with the composition within five minutes at a temperature of 20° C. A total kill is expected with a longer exposure time, a higher concentration of the germicidal compound, and/or a higher temperature.

In one aspect, a germicidal composition may include a germicidally effective amount of a propanedial compound in an aqueous solution or other suitable diluent. As demonstrated in Example 4, a composition including from about 0.3 to 0.4% or more phenyl-propanedial is effective to achieve a total kill of *Mycobacterium terrae* bacteria within 60 minutes at a temperature of 20° C. A composition including from about 0.4 to 0.7% or more phenyl-propanedial is effective to achieve a total kill of the bacteria within 15 minutes at the same temperature. A composition including about 1% or more phenyl-propanedial is able to kill more than 4 logs of the bacteria in just 5 minutes at the same temperature. Moreover, as demonstrated in Example 5, a composition including about 2.3% or more 4-pyridinyl-propanedial or about 2.1% or more 3-(1-formyl-2-oxoethyl)-2-nitro-benzoic acid is effective to kill at least $1\times10^4$ bacteria of *Mycobacterium terrae* in contact with the composition within five minutes at a temperature of 20° C.

In other aspect, the composition at an in-use germicidally effective concentration may include between 0.1% to a saturation concentration, or from 0.3% to a saturation concentration of the germicidal compound. A water miscible co-solvent, such as methanol, ethanol, isopropanol, glycols, tetrahydrofuran, dimethylsulfoxide, or dioxane, among others, may be used to increase the solubility of the compound, if desired. A higher concentrations may be used for shipping the composition to the point of use, and then composition may be diluted with water to the desired use concentration.

The composition containing the germicidally effective amount of the compound may be used for disinfection or sterilization. A method according to one embodiment may include disinfecting a surface by contacting the surface with the composition for a period of time and at a temperature effective to achieve disinfection or sterilization of the surface. The surface may be contacted with the composition by immersion, spraying, or coating, for example. The propanedial compounds generally are non-staining, and have generally low volatilities.

III. Germidical α-Hydroxy Sulfonate Aldehydes

The inventors have discovered a number of novel, water-soluble, α-hydroxy sulfonate aldehyde compounds, which have α-hydroxy sulfonate groups [—$CH(OH)SO_3^-$], and aldehyde groups (—CHO), and which have germicidal efficacy. An embodiment of the invention comprises a water-soluble compound having a substantially high solubility, for example at least 5 (w/v) % in water. Specific examples of the novel compounds are listed in Table 7.

TABLE 7

| Compound | Name |
|---|---|
| 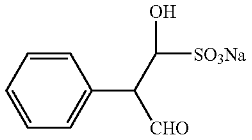 | 1-hydroxy-3-oxo-2-phenyl-propane-1-sulfonic acid, sodium salt |
| 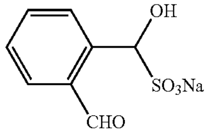 | (2-formyl-phenyl)-hydroxy-methane sulfonic acid, sodium salt |
| 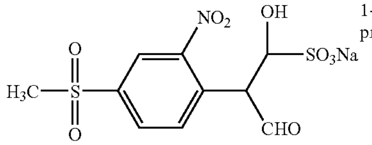 | 1-hydroxy-2-(4-methanesulfonyl-2-nitro-phenyl)-3-oxo-propane-1-sulfonic acid, sodium salt |
| 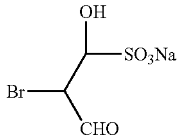 | 2-bromo-1-hydroxy-3-oxo-propane-1-sulfonic acid, sodium salt |

TABLE 7-continued

| Compound | Name |
|---|---|
| 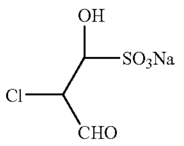 | 2-chloro-1-hydroxy-3-oxo-propane-1-sulfonic acid, sodium salt |
| 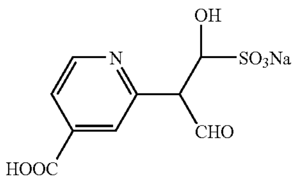 | 2-(1-formyl-2-hydroxy-2-sulfo-ethyl)-isonicotinic acid, sodium salt |
| 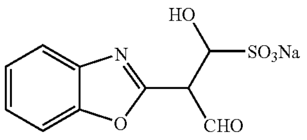 | 2-benzooxazol-2-yl-1-hydroxy-3-oxo-propane-1-sulfonic acid, sodium salt |
| 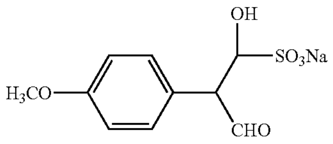 | 1-hydroxy-2-(4-methoxy-phenyl)-3-oxo-propane-1-sulfonic acid, sodium salt |

In each of the above compounds, the sulfonate group (—$SO_3^-$) and the hydroxyl group (—OH) are connected to the same carbon. This moiety, including the hydroxyl group, the sulfonate group, and the single carbon separating them, may be referred to herein as a hydroxyl-methane sulfonate group or moiety. The use of sodium ions ($Na^+$) is not required, and other ions may also optionally be employed. The compounds may also have an acid form, generally at a relatively low pH. Often, it may be appropriate to convert the acid form to an ionized form prior to use in disinfection or sterilization. A method may include increasing a pH of a medium containing the acid form of the compounds, for example by adding a base, in order to convert the compounds from the acid form to the ionized form. In many of the above compounds, the α-hydroxy sulfonate group is proximate the aldehyde group. In each of the compounds, the α-hydroxy sulfonate group is separated from the aldehyde group by less than four carbon atoms. In a majority of the compounds, as with the 1-hydroxy-3-oxo-2-phenyl-propane-1-sulfonic acid salt, and other compounds that may be derived from a 1,3-propanedialdehyde structure, the α-hydroxy sulfonate group is separated from the aldehyde group by only two carbon atoms.

The inventors have discovered that the compounds have germicidal activity and have developed new uses of the compounds for disinfection or sterilization. Typically, the compound or a mixture of the compounds will be used to form a germicidal composition including a germicidally effective amount of the compound or mixture as an active ingredient, and a diluent, such as water. Due in part to the sulfonate group, which includes a hydroxyl group, the compounds are substantially soluble in water. Typically, the compounds are more soluble in water than a corresponding compound in which the sulfonate group is replaced with an aldehyde group. Often, the solubility in water is greater than 5 (w/v) %. The substantial solubility in water may facilitate dissolution of the compounds into water and other polar solvents. Due to the increased water solubility the compounds may be employed at higher concentrations in water than typical for common dialdehyde germicides. The compounds are also generally non-volatile. Other ingredients that may be included in the composition include pH-adjusters, buffer salts, chelating agents, corrosion inhibitors, surfactants, alcohols, or other miscible solvents, fragrances, coloring agents, and the like. The composition may be used to kill bacteria or to disinfect surfaces by contacting the bacteria or the surfaces with the composition for a period of time and at a temperature sufficient to achieve the kill or disinfection.

In Examples 6-7, which follow, several germicidal solutions containing the compounds listed in Table 7 were tested to determine their effectiveness in killing at least $1\times10^6$/mL of *Mycobacterium terrae* bacteria using a bacterial suspension test. The pH of the solution was not adjusted. The tests were conducted at a temperature of about 20° C. (room temperature). The results are presented in terms of log reductions/mL.

EXAMPLE 6

Germicidal solutions containing various concentrations of 1-hydroxy-3-oxo-2-phenyl-propane-1-sulfonic acid sodium salt were tested at exposure times ranging from 5 to 60 minutes. The results are shown in Table 8.

TABLE 8

| Concentration | Log Reductions/mL (20° C.) | | | | | | |
|---|---|---|---|---|---|---|---|
| (%) | 5 min | 10 min | 15 min | 20 min | 25 min | 30 min | 60 min |
| 0.6 | 2.1 | Not Tested | 2.4 | 2.5 | 2.9 | 3.5 | Total Kill |
| 2.5 | Not Tested | Total Kill | Not Tested | Not Tested | Not Tested | Total Kill | Not Tested |
| 9.4 | Not Tested | Not Tested | Not Tested | Not Tested | Not Tested | Total Kill | Not Tested |

The results show that, under the test conditions, the 1-hydroxy-3-oxo-2-phenyl-propane-1-sulfonic acid sodium salt has germicidal efficacy and that a concentration of about 0.6% is effective to achieve a total kill of more than $1\times10^6$ of the *Mycobacterium terrae* bacteria in 60 minutes at a temperature of 20° C. The results also show that a concentration of 2.5% or higher is effective to achieve a total kill in only 10 minutes.

EXAMPLE 7

Germicidal solutions containing various compounds from Table 7 were tested at exposure times of 30 to 120 minutes at a temperature of 20° C. The results are shown in Table 9.

TABLE 9

| Compound | Concentration (%) | Log Reductions/mL (20° C.) 30 min | 60 min | 120 min |
|---|---|---|---|---|
| (2-Formyl-phenyl)-hydroxy-methane sulfonic acid salt | 8.9 | 2.0 | 3.5 | 5.7 |
| 1-Hydroxy-2-(4-methanesulfonyl-2-nitro-phenyl)-3-oxo-propane-1-sulfonic acid salt | 14 | Total Kill | Not Tested | Not Tested |
| 2-Bromo-1-hydroxy-3-oxo-propane-1-sulfonic acid salt | 9.5 | Total Kill | Not Tested | Not Tested |
| 2-Chloro-1-hydroxy-3-oxo-propane-1-sulfonic acid salt | 7.9 | Total Kill | Not Tested | Not Tested |
| 2-(1-Formyl-2-hydroxy-2-sulfo-ethyl)-isonicotinic acid salt | 11.1 | Total Kill | Not Tested | Not Tested |
| 2-Benzooxazol-2-yl-1-hydroxy-3-oxo-propane-1-sulfonic acid salt | 11.1 | Not Tested | 5.0 | Total Kill |
| 1-Hydroxy-2-(4-methoxy-phenyl)-3-oxo-propane-1-sulfonic acid salt | 10.5 | Total Kill | Not Tested | Not Tested |

The results show that, under the test conditions, all of the compounds have germicidal efficacy. All of the compounds except (2-formyl-phenyl)-hydroxy-methane sulfonic acid salt were able to achieve a total kill of more than $1\times10^6$ of the *Mycobacterium terrae* bacteria within 120 minutes (two hours) at a temperature of 20° C. All compounds except (2-formyl-phenyl)-hydroxy-methane sulfonic acid salt, and 2-benzooxazol-2-yl-1-hydroxy-3-oxo-propane-1-sulfonic acid salt, were able to achieve a total kill within 30 minutes.

In one aspect, a germicidal composition may include a germicidally effective amount of one or more of the compounds in an aqueous solution or other suitable diluent. Based on the data provided in the examples, the amount may be effective to kill at least $1\times10^6$ *Mycobacterium terrae* bacteria in contact with the composition within two hours, one hour, 30 minutes, or 10 minutes, with a bacterial suspension test at a temperature of 20° C. The listed concentrations in the examples are not required, and alternatively, lower amounts may be provided if longer times or higher temperatures are employed. In another aspect, the composition may include from 0.1% to a saturation amount of the compound. For some compounds, depending on the saturation amount, it may be from about 0.1% to 15%.

The composition containing the germicidally effective amount of the compound may be used for disinfection or sterilization. A method according to one embodiment may include disinfecting a surface by contacting the surface with the composition for a period of time and at a temperature effective to achieve disinfection or sterilization of the surface. The surface may be contacted with the composition by immersion, spraying, or coating, for example.

Other embodiments of the invention include a method of making such a compound, or a compound produced by such a method, or a germicidal composition including such a compound, or a method of using such a compound for disinfection or sterilization. A method, according to one embodiment, may include providing a polyaldehyde compound (for example a dialdehyde compound), and forming a water-soluble compound (more soluble than the dialdehyde compound) having an aldehyde group and an α-hydroxy sulfonate group, from the dialdehyde compound. Producing the water-soluble compound may include combining appropriate amounts, for example nearly equal molar amounts, of sodium bisulfate with the polyaldehyde, and inducing reaction. Suitable dialdehyde compounds for making the compounds include, but are not limited to, phenyl-propanedial, phthalaldehyde, [4-(methylsulfonyl)-2-nitrophenyl]-propanedial, bromo-propanedial, chloro-propanedial, and 2-(1-formyl-2-oxo-ethyl)-isonicotinic acid, 2-benzoxazolyl-propanedial, and 4-methoxyphenyl-propanedial, and combinations thereof.

Several of these compounds, such as phthalaldehyde, are known to have germicidal efficacy. The inventors have discovered that replacing one of the aldehyde groups of a polyaldehyde with a hydroxyl-methane sulfonate group, that is an α-hydroxy sulfonate group, does not eliminate the germicidal efficacy but allows increasing the water solubility. Broadly stated, an embodiment of the invention includes a novel germicidal compound having a structure similar to that of a known germicidal polyaldehyde (e.g., a dialdehyde), such as, but not limited to, phthalaldehyde, but in which one of the aldehyde groups of the dialdehyde is replaced to produce an α-hydroxy sulfonate containing a hydroxyl-methane sulfonate group. In one aspect, the replaced aldehyde group may be reacted with a bisulfite (e.g., sodium bisulfite, $NaHSO_3$), sulfite (e.g., sodium sulfite, $Na_2SO_3$), or metabisulfite (e.g., sodium metabisulfite, $Na_2S_2O_5$) in order to convert the aldehyde to the a-hydroxy sulfonate. The use of sodium is not required and other ions (e.g., potassium) may also optionally be employed. Another aldehyde group or moiety of the compound may be retained or unreacted in the α-hydroxy sulfonate. This allows novel germicidal compounds that have germicidal efficacy along with enhanced water solubility and lower volatility. The examples of this section demonstrate significant germicidal efficacy for a variety of compounds having diverse structures and chemical properties (e.g., aromatic vs. non-aromatic, halogenated vs. non-halogenated, acidic vs. non-acidic, etc). This indicates the broad applicability of the method for producing germicidal compounds.

IV. Germicidal Compositions Including Phthalaldehyde with One or More of its Isomers Isophthalaldehyde and Terephthalaldehyde The inventors have discovered a number of novel germicidal compositions including phthalaldehyde(1,2-benzenedicarboxaldehyde) mixed with one or more of its isomers isophthalaldehyde(1,3-benzenedicarboxaldehyde) and terephthalaldehyde(1,4-benzenedicarboxaldehyde). For convenience, we will abbreviate phthalaldehyde as OPA, isophthalaldehyde as EPA, and terephthalaldehyde TPA. The structures of OPA, IPA, and TPA are given in Table 10.

TABLE 10

| Compound | Name |
| --- | --- |
| 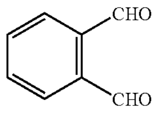 | phthalaldehyde (OPA) |
| 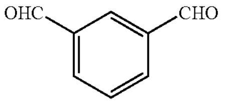 | isophthalaldehyde (IPA) |
| 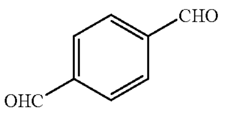 | terephthalaldehyde (TPA) |

OPA, IPA, and TPA are commercially available from numerous sources including Sigma-Aldrich, Alfa Aesar, and Fluka, among others.

A germicidal composition, according to one embodiment of the invention, may include a diluent, such as those discussed elsewhere herein, OPA, and IPA. The composition generally has an unexpectedly enhanced germicidal efficacy due to an apparent synergistic effect between the OPA and the IPA. Additionally, the composition generally has the novel, unexpected, and superior property that it stains less than a composition consisting essentially of OPA at the same concentration (for example OPA and diluent alone without the IPA). This is due to more than just "dilution" of the staining properties of the OPA and may be due to an unexpected or synergistic effect. Other potentially advantageous properties of the composition include that it is nearly odorless and is generally compatible with stainless steel, as well as other materials commonly used to form medical devices. The use of the IPA may offer other potential advantages, such as reduced toxicity relative to OPA.

EXAMPLE 8

Several germicidal solutions were tested to determine their effectiveness in killing at least $1\times10^6$/mL of *Mycobacterium terrae* bacteria using a bacterial suspension test. Germicidal solutions containing from 0.08 to 0.28% of OPA, 0.3% IPA diluted in 20% isopropanol, or 0.14% OPA plus 0.2% IPA were tested at exposure times of 5 and 30 minutes. The pH of the solution was not adjusted. The tests were conducted at a temperature of about 20° C. (room temperature). The results are presented in terms of log reductions/mL in Table 11.

TABLE 11

| | Log Reductions/mL (20° C.) | |
| --- | --- | --- |
| Composition | 5 min | 30 min |
| 0.08% OPA | Not Tested | 3.1 |
| 0.10% OPA | Not Tested | 3.4 |
| 0.14% OPA | 4.8 | 5.8 |
| 0.28% OPA | 5.5 | Not Tested |
| 0.3% IPA[a] | Confluent | Not Tested |
| 0.14% OPA + 0.2% IPA | Total Kill | Not Tested |

[a]Dissolved in 20% isopropanol.

The results show that, under the test conditions, germicidal compositions including about 0.14% OPA plus 0.2% IPA, or higher concentrations of the active ingredients, are effective to achieve a total kill of the bacteria within 5 minutes at a temperature of 20° C. The results also show that mixing the OPA and the IPA enhances the germicidal efficacy or that there is a germicidal synergy between OPA and IPA. Note that a total kill was not achieved when about twice the concentration of OPA (0.28%) was employed for 5 min. Also note that a higher concentration of EPA (0.3%) didn't have a significant kill (confluent). This enhancement or germicidal synergy for a mixture of OPA and IPA is unexpected and significant.

EXAMPLE 9

Three solutions containing either OPA, IPA, or a combination of OPA and IPA, were tested to determine their staining properties. Skin from the ear of a pig was acquired from an Asian Food Supermarket, in Orange County, California. The pigskin was cut to convenient sizes and the cut pieces were laid flat on a surface. About 10 μL of the solutions were placed on the surface of the pigskin. The drops were allowed to remain on the pigskin for about 24 hours at room temperature. Then the staining properties of each of the solutions were assessed by comparing the color of the pigskin at the location of each drop to the color of the surrounding untreated pigskin. The results are shown in Table 12.

TABLE 12

| Composition | Staining Results |
| --- | --- |
| 0.14% OPA | Dark Staining |
| 0.20% IPA | Non-Staining |
| 0.14% OPA + 0.20% IPA | Nearly Non-Staining |

The results show that, under the test conditions, the OPA solution was dark staining, the EPA solution was non-staining, and the OPA plus IPA solution was nearly non-staining. These results show that the IPA reduces the staining property of the OPA.

A germicidal composition, according to another embodiment of the invention, may include a diluent, such as those discussed elsewhere herein, a germicidally effective amount of OPA, IPA, and TPA. The composition including the TPA has unexpectedly enhanced germicidal efficacy over a composition including only OPA, due to an apparent synergistic effect between the TPA plus IPA and the OPA. Additionally, the composition generally has the novel, unexpected, and superior property that it stains less than a composition including the same concentration of OPA alone. In fact, the inventors have observed that the TPA further reduces the staining caused by the OPA over a mixture of OPA plus IPA. This is due to more than just "dilution" of the staining properties of the OPA. Other potentially advantageous properties of the composition include that it is nearly odorless and is generally compatible with materials used for medical devices.

EXAMPLE 10

Several germicidal solutions were tested to determine their effectiveness in killing at least $1\times10^6$/mL of *Mycobacterium terrae* bacteria using a bacterial suspension test. Germicidal solutions containing TPA or mixtures of TPA with OPA, IPA, or both, were tested at an exposure time of 5 minutes and a temperature of 20° C. The pH of the solution was not adjusted. The tests were conducted at a temperature of about 20° C. (room temperature). The results are presented in terms of log reductions/mL in Table 13.

TABLE 13

| Composition | Log Reductions/mL (20° C., 5 min) |
|---|---|
| 0.2% TPA[a] | Confluent |
| 0.1% TPA + 0.1% OPA | Confluent |
| 0.1% TPA + 0.2% IPA | Confluent |
| 0.1% TPA + 0.2% IPA + 0.1% OPA | Total Kill |

[a]Dissolved in 20% isopropanol.

The results show that, under the test conditions, germicidal compositions including about 0.1% TPA, plus 0.2% IPA, plus 0.1% OPA, or higher concentrations, are effective to achieve a total kill of the bacteria within 5 minutes at a temperature of 20° C. The results also show that a mixture of TPA and IPA enhances the germicidal efficacy of OPA or that there is a germicidal synergy. That is, the composition including TPA, IPA, and OPA has unexpectedly enhanced germicidal efficacy over a composition including only OPA. Note from Example 8 that a 0.1% OPA concentration was not effective to achieve a total kill. Note also that a mixture of 0.1% TPA plus 0.2% IPA didn't have a significant kill (confluent). This enhancement or germicidal synergy is unexpected and significant.

Staining experiments performed as described above indicate that the OPA, EPA, and TPA composition generally has the novel, unexpected, and superior property that it stains less than a composition including the same concentration of OPA alone. In fact, the data also indicates that the TPA further reduces the staining caused by the OPA over a mixture of OPA plus IPA.

In general, each of the compositions discussed above may include a germicidally effective amount of OPA. Phthalaldehyde may be used in the compositions at an in-use concentration of from 0.025% to 2.0%, or 0.1 to 1% by weight. Higher concentrations, for example, up to 5% may be used if desired. Higher concentrations of phthalaldehyde may be used for shipping the composition to the point of use, and then composition may be diluted with water to the desired use concentration. The solubility of phthalaldehyde in water is about 5% by weight, which may be increased by including a water-miscible, or at least more water-soluble, co-solvent. Suitable solvents include methanol, ethanol, isopropanol, n-butanol, t-butanol, glycols, tetrahydrofuran, dimethylsulfoxide and dioxane, among others In one aspect, due to the enhancement by the EPA, the germicidally effective amount of OPA may be less than that needed when OPA is employed without IPA. Various estimates of this upper bound on the germicidally effective amount for OPA are known in the arts. Based on the results presented in U.S. Pat. No. 4,971,999, the germicidally effective amount of OPA when employed with EPA may be about 0.25%, or less, to be effective against *Mycobacterium tuberculosis, Mycobacterium bovis* BCG, and Poliovirus Type I in 10 minutes or less at a temperature of 20° C. Alternatively, the germicidally effective amount of OPA when employed with IPA may be about 0.25%, or less, to be effective against *Bacillus subtilis* and *Clostridium sporogenes* spores in 24 hours at a temperature of 20° C. As yet another option, the germicidally effective amount of OPA when employed with IPA may be about 1%, or less, to achieve sterilization in 10 hours.

In another aspect, the germicidally effective amount may be effective to kill at least $1\times10^6$ *Mycobacterium terrae* bacteria in contact with the composition in less than 5 minutes, with a bacterial suspension test at a temperature of 20° C. As demonstrated in Example 8, a composition including about 0.14% OPA plus 0.2% IPA, or higher concentrations, are effective to achieve a total kill of the bacteria within 5 minutes at a temperature of 20° C. As demonstrated in Example 9, a composition including about 0.1% TPA, plus 0.2% IPA, plus 0.1% OPA, or higher concentrations, are effective to achieve a total kill of the bacteria within 5 minutes at a temperature of 20° C.

In one aspect, IPA, TPA, or a combination of IPA and TPA, may be employed in an amount that is effective to enhance the efficacy of or reduce a staining property of the OPA to a desired extent. At least to an extent, the more IPA, TPA, or IPA plus TPA, the greater the enhancement of the efficacy or the reduction of the staining by the OPA. A relatively small amount or proportion of IPA, TPA, or IPA plus TPA, may be employed to achieve a relatively smaller effect, or a relatively larger amount or proportion of one or more of these components may be employed to achieve a relatively larger effect. In various aspects, the molar or weight ratio of IPA to OPA is typically from about 0.1:1 to about 10:1; often between about 0.2:1 to about 5:1, and may be between about 0.5:1 to about 2:1. Likewise, in various aspects, the molar or weight ratio of TPA to OPA is typically from about 0.1:1 to about 10:1; often between about 0.2:1 to about 5:1, and may be between about 0.5:1 to about 2:1.

Table 14 summarizes the germicidal efficacies and staining characteristics of OPA, IPA, TPA, and mixtures of OPA with IPA and IPA plus TPA. As shown, OPA has good germicidal efficacies, but tends to stain certain surfaces. IPA and TPA do not stain but have much poorer germicidal efficacies. The inventors have discovered that compositions including OPA plus IPA, or OPA plus IPA plus TPA, have good germicidal efficacies and reduced staining.

TABLE 14

| Composition | Staining | Germicidal Efficacy |
|---|---|---|
| OPA | + | Good |
| IPA | − | Poor |
| TPA | − | Poor |
| OPA + IPA | − | Good |
| OPA + IPA + TPA | − | Good |

The compositions discussed above may be used for disinfection or sterilization with reduced staining of devices and other surfaces. A method, according to one embodiment, may include disinfecting a surface by contacting the surface with the composition for a period of time and at a temperature effective to achieve disinfection or sterilization of the surface.

V. Germicidal Compositions Including Phenyl-Propanedial and One or More Aromatic Dialehydes The inventors have discovered novel compositions including phenyl-propanedial (also known as phenyl-molonaldehyde or simply PMA) and one or more aromatic dialdehydes, such as isophthalaldehyde (IPA), or a combination of IPA and terephthalaldehyde (TPA). The IPA, and the combination of IPA and TPA, unexpectedly and significantly enhance the germicidal efficacy of the phenyl-propanedial composition.

A germicidal composition, according to one embodiment of the invention, may include a diluent, such as those discussed elsewhere herein, a germicidally effective amount of phenyl-propanedial, and IPA to enhance the germicidal efficacy of the phenyl-propanedial. Alternatively, the IPA may be replaced by a combination of IPA and TPA. A germicidal composition, according to another embodiment of the invention, may include a diluent, a germicidally effective amount of phenyl-propanedial, and a combination of IPA and TPA to enhance the germicidal efficacy of the phenyl-propanedial. As demonstrated in Example 11 below, these compositions generally have unexpectedly enhanced germicidal efficacies due to apparent synergistic effects between the phenyl-propanedial and the IPA, or the combination of IPA and TPA. Other potentially advantageous properties of the compositions include that they are nearly odorless, do not stain significantly, and have good compatibility with stainless steel and a variety of other materials.

EXAMPLE 11

Several germicidal solutions containing PMA, PMA plus IPA, and PMA plus IPA and TPA were tested to determine their effectiveness in killing at least $1\times10^6$/mL of *Mycobacterium terrae* bacteria using a bacterial suspension test. The tests were conducted at a temperature of about 20° C. (room temperature). The pH of the solution was not adjusted. The results are presented in terms of log reductions/mL in Table 15.

TABLE 15

| | Log Reductions/mL (20° C.) | | | | |
|---|---|---|---|---|---|
| Composition | 5 min | 10 min | 15 min | 30 min | 60 min |
| 0.22% PMA | Not Tested | Not Tested | Not Tested | Not Tested | 2.1 |
| 0.33% PMA | Not Tested | Not Tested | Not Tested | 2.1 | 3.7 |
| 0.44% PMA | Not Tested | Not Tested | Not Tested | 2.5 | Total Kill |
| 0.66% PMA | <2.5 | 2.5 | Total Kill | Not Tested | Not Tested |
| ~1% PMA | 4.5 | Not Tested | Not Tested | Not Tested | Not Tested |
| 0.3% IPA[a] | Confluent | Not Tested | Not Tested | Not Tested | Not Tested |
| ~1% PMA + 0.2% IPA[a] | 5.3 | Not Tested | Not Tested | Not Tested | Not Tested |
| 0.2% IPA + 0.1% TPA | Confluent | Not Tested | Not Tested | Not Tested | Not Tested |
| 0.68% PMA + 0.2% IPA + 0.1% TPA | >6.0 | Not Tested | Not Tested | Not Tested | Not Tested |

[a]Dissolved in 20% isopropanol.

The results show that, under the test conditions, the IPA and the combination of the IPA and TPA, both enhance the germicidal efficacy of the PMA. A composition including 0.68% PMA, 0.2% IPA, 0.1% TPA, or a higher concentration, are effective to kill at least $1\times10^6$ *Mycobacterium terrae* bacteria in contact with the composition in less than 5 minutes, with a bacterial suspension test at a temperature of 20° C. Such results are significantly and unexpectedly better than those for a composition consisting essentially of PMA diluted to the same concentration (that is without the IPA or IPA and TPA).

In general, each of the compositions discussed above may include a germicidally effective amount of the phenyl-propanedial. For example, the phenyl-propanedial may be used in the compositions at an in-use concentration of from 0.025% to a saturation concentration. The solubility of phenyl-propanedial in water is about 1%, which may be increased by including a water-miscible, or at least more water-soluble, co-solvent. If desired, a higher concentration of the germicidal compound may be used for shipping the composition to the point of use, and then composition may be diluted with water to the desired use concentration.

In one aspect, IPA, or IPA plus TPA, may be employed in an amount that is effective to enhance the efficacy of the phenyl-propanedial to a desired extent. At least to an extent, the more IPA, or combined amount of IPA plus TPA, the greater the enhancement. A relatively small amount or proportion of IPA, or IPA plus TPA, may be employed to achieve a relatively smaller effect, or a relatively larger amount or proportion of one or more of these components may be employed to achieve a relatively larger effect. In various aspects, the molar or weight ratio of IPA, or IPA plus TPA, to phenyl-propanedial is typically from about 0.1:1 to about 2:1. Often, the ratio is at least about 0.2:1.

VI. Germicidal Compositions Including α-Hydroxy Sulfonate Aldehydes One or More Aromatic Dialdehydes The inventors have further discovered novel compositions including (2-formyl-phenyl)-hydroxy-methane sulfonate and one or more aromatic dialdehydes, such as phthalaldehyde (OPA), isophthalaldehyde (IPA), terephthalaldehyde (TPA), and combinations thereof. The inventors have found that the compositions may have unexpected and significant properties, such as enhanced germicidal efficacies, or reduced staining characteristics.

A germicidal composition, according to one embodiment of the invention, may include (2-formyl-phenyl)-hydroxy-methane sulfonate, and one or more aromatic dialdehydes selected from the group consisting of OPA, IPA, TPA, and combinations thereof. As demonstrated in Example 12, compositions including IPA, TPA, or IPA plus TPA, have enhanced germicidal efficacies. The inventors have also found that (2-formyl-phenyl)-hydroxy-methane sulfonate is able to reduce a staining property of OPA.

EXAMPLE 12

Several germicidal compositions containing mixtures of (2-formyl-phenyl)-hydroxy-methane sulfonate (H-SULF) with either OPA, IPA, TPA, or a combination of IPA and TPA, were tested to determine their effectiveness in killing at least $1\times10^6$/ml of *Mycobacterium terrae* bacteria using a bacterial suspension test. The tests were conducted at a temperature of about 20° C. (room temperature). The results are presented in Table 16 in terms of log reductions/mL.

TABLE 16

| Composition | Log Reductions/mL (20° C., 5 min) |
|---|---|
| 9.1% H-SULF | Confluent |
| 0.9% H-SULF + 0.5% OPA | Total Kill |
| 1.1% H-SULF + 0.3% IPA | Total Kill |
| 2.3% H-SULF + 0.3% IPA | Total Kill |
| 4.5% H-SULF + 0.3% IPA | Total Kill |
| 9.1% H-SULF + 0.1% TPA | 4.5 |
| 1.1% H-SULF + 0.2% IPA + 0.1% TPA | Total Kill |
| 2.3% H-SULF + 0.2% IPA + 0.1% TPA | Total Kill |

The results show that compositions including (2-formyl-phenyl)-hydroxy-methane sulfonate (H-SULF) with OPA, IPA, TPA, and a combination of IPA and TPA, each have enhanced germicidal efficacies. A composition including a relatively high concentration of about 9.1% (2-formyl-phenyl)-hydroxy-methane sulfonate without any dialdehyde was found to be confluent after 5 minutes. In contrast, several compositions including one or more of the previously mentioned aromatic dialdehydes had significantly and unexpectedly better germicidal efficacies.

A first composition including 0.9% or higher (2-formyl-phenyl)-hydroxy-methane sulfonate and 0.5% OPA was determined to be effective to achieve a total kill of the bacteria within 5 minutes. Additionally, a stain test indicated that the composition stained less than a composition consisting essentially OPA diluted to the same concentration, that is without the (2-formyl-phenyl)-hydroxy-methane sulfonate. A second composition including 1.1% or higher (2-formyl-phenyl)-hydroxy-methane sulfonate and 0.25% IPA was determined to be effective to achieve a total kill of the bacteria within 5 minutes. A third composition including 9.1% or higher (2-formyl-phenyl)-hydroxy-methane sulfonate and 0.1% TPA was determined to be effective to achieve a log reduction of about 4.5 within 5 minutes. A fourth composition including 1.1% or higher (2-formyl-phenyl)-hydroxy-methane sulfonate, 0.2% IPA, and 0.1% TPA was determined to be effective to achieve a total kill of the bacteria within 5 minutes. Such increases in the efficacies, as well as the reduction in the staining of OPA, are significant and unexpected.

VII. Suspension Test

This example demonstrates the well-known bacteria suspension test procedure used to make the determination of effectiveness. In this test method, 9 mL of the germicide to be tested is placed in a tube, put into a water bath and allowed to come to the desired temperature. One mL of the test organism, including at least 7 logs/mL of *Mycobacterium terrae* bacteria, is added to the 9 mL of the germicide to be tested. The dilution resulted in at least 6 logs/mL of the bacteria in the mixture. It will be appreciated by those skilled in the art that other concentrations may be utilized by proper dilution and accounting.

At appropriate time intervals, 1 mL aliquots of the germicide-cell suspension were removed and added directly into 9 mL of a 1% glycine solution (neutralizer) and mixed thoroughly to neutralize the germicide in the transferred suspension. The glycine solution was prepared from solid glycine, which is available from VWR Scientific Products, among others. The above-identified 10 mL neutralized solution was then poured through a membrane filter having an average pore size of 0.45 micrometers. The filter was then rinsed twice with at least 150 mL of the 1% glycine solution per rinse. The filter was then placed on an agar plate and incubated for twenty-one days at 37° C. In the above procedure, if dilution was needed, then the 1 mL germicidal-cell suspension was diluted in 99 mL of a phosphate buffer before addition to the 9 mL of the 1% glycine solution. The phosphate buffer was DiLu-LoK™ Butterfields Phosphate Buffer, available from Hardy Diagnostics, of Santa Maria, Calif.

The surviving colonies are then counted. The data is plotted as $S/S_o$ vs. time. $S_o$ is the initial count of the bacteria in the above 10 mL solution which is at least $10^6$ bacteria/mL, and S is the surviving bacteria from the above filter on the agar plate. The results of the experiments were presented in terms of log reductions. Log reduction is the difference between $\log(S_o)$ and $\log(S)$. As one example, if $\log(S_o)=6.2$, and if there were 100 survivors, then the $\log(S)=2$, and the log reduction was reported as 4.2.

VIII. Synthesis of Germicidal Compounds

A. Synthesis of 4-Substituted Phthalaldehydes

This section shows how to synthesize 4-chloro-benzene-1, 2-carbaldehyde (Compound 3) by using 4-chloro-o-xylene (Compound 1) as a starting material. The synthesis proceeds according to the following two serial reactions:

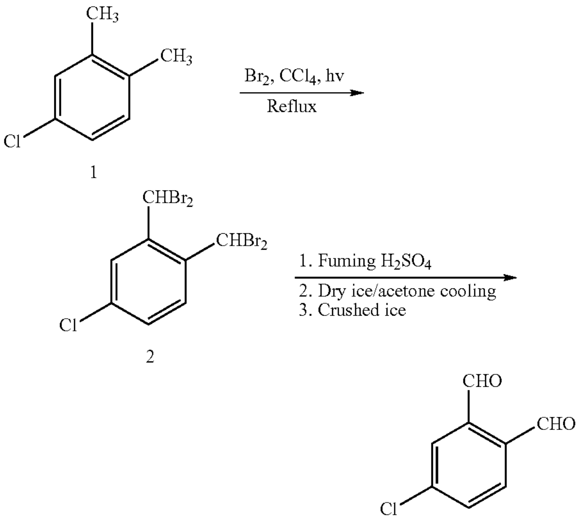

1 2 3

In the first reaction, Compound 1 is brominated by reflux with carbon tetrachloride with light irradiation to form 4-chloro-1,2-bis(dibromomethyl)benzene (Compound 2). In the second reaction, Compound 2 is first reacted with fuming sulfuric acid to form a complex, and then hydrolyzed at dry ice/acetone temperature to produce Compound 3.

1. Bromination.

First, let us begin with discussing the first reaction in greater detail. Compound 1 was obtained from Aldrich at a purity of ≧98%. Five grams of Compound 1 and about 200 mL of carbon tetrachloride ($CCl_4$) were added into a 250 mL three-neck round bottom flask equipped with a magnetic stirring bar, a 200 mL additional funnel, a condenser, and a stopper. The outlet of the condenser was connected via Tygon tubing to a beaker filled with a saturated sodium bicarbonate ($NaHCO_3$) solution to trap hydrogen bromide (HBr) generated during the reaction.

The solution in the flask was first heated to reflux in a silicon oil bath at the boiling temperature of carbon tetrachloride. Liquid bromine was then added dropwise from the additional funnel. The bromine addition rate was manually controlled in order to control the concentration of the bromine in the solution in the flask. Additional bromine was added if the color of the solution became lighter, or colorless. Two 250 W tungsten lamps were used to irradiate the mixture to enhance the bromination. If desired, the progression of the reaction may be monitored by sampling the solution, and then using a gas chromatograph (GC) to determine the amount of Compound 2 in the sample. This reaction was allowed to proceed for about 6 hours.

Then, the carbon tetrachloride was removed at normal pressure by distillation at 130° C. until about 180 mL of the carbon tetrachloride was removed. Then, a series of five additions of methanol, of about 20 mL each, were added to the residual in the flask to azeotropically remove residual carbon tetrachloride by distillation at 130° C. On the final distillation, when about 20 mL of solution remained in the flask, the solution was cooled to room temperature. Then, the remaining solvent was removed at 40° C. with a rotary evaporator at about 10 mmHg to produce a solid in the bottom of the flask. The solid was boiled in about 150 mL of hexane until dissolved, and the resulting solution was filtered. The filtrate was allowed to cool down to room temperature to form white needle crystals of Compound 2. The crystals were filtered and washed with about 20 mL of cold hexane. About 12 grams of the white needle crystals of Compound 2 were obtained. GC indicated a purity of 99% (yield~72%).

2. Hydrolysis

Next, let us discuss the hydrolysis reaction in greater detail. About 6.4 grams of Compound 2 were ground into a powder and added to a dry 100 mL round bottom flask equipped with a magnetic stirring bar. About 20 mL of fuming sulfuric acid (obtained from Fisher Scientific AC419975000, Oleum, 20% free $SO_3$) was poured into the flask while stirring with a magnetic stirring bar. The mixture was stirred at room temperature for about 1 hour. During the hour the powder dissolved and the solution gradually became dark brownish in color.

Then, the solution with magnetic stirring bar was poured into a 100 mL beaker immersed in a dry ice/acetone bath. About 25 g of crushed ice was gradually added to the brownish solution with stirring so that the temperature of the solution did not increase rapidly. After the addition of the crushed ice, the temperature of the solution was gradually allowed to increase to room temperature. Then, the solution was timely extracted with two serial additions of about 100 mL of ethyl acetate. Following this extraction, the organic phase was extracted with three 50 mL solutions of 5% sodium carbonate ($Na_2CO_3$). After the extraction with the sodium carbonate solution, the organic phase was again extracted with three 50 mL solutions of saturated sodium chloride (NaCl). These extractions may help to remove impurities, such as compounds containing carboxylic acid groups, or oxidized aldehyde. The resultant organic phase was dried over about 10 g of sodium sulfate ($Na_2SO_4$) overnight at room temperature. After drying, the remaining solvent was removed at 40° C. by rotary evaporator at about 10 mmHg to obtain a yellow solid. The yellow solid was boiled in about 30 mL of hexane until dissolved, and then was filtered. The filtrate was allowed to cool to room temperature to give white crystals. About 1.7 g of the white crystals were obtained (GC purity 99%, yield=72%).

The inventors have also synthesized other 4-halo-OPA's, such as 4-bromo-OPA and 4-fluoro-OPA, by procedures similar to that discussed above for 4-chloro-OPA. In the case of 4-fluoro-OPA, which is a liquid, column chromatograph was used for separation. In the case of 4-bromo-OPA, as in the above-described case of 4-chloro-OPA, crystallization and re-crystallization were used for the separation. Various similarities and differences are listed in Table 16.

TABLE 16

| | Condition Variables | 4-Chloro-OPA | 4-Bromo-OPA | 4-Fluoro-OPA |
|---|---|---|---|---|
| Bromination | Bromination Time | ~6 hours | ~2 hours | ~6 hours |
| | Separation | Normal crystallization | Use hot hexane to isolate 4-bromo-1,2-bis(dibromomethyl) benzene from 3-bromo-1-bromomethyl-2-dibromomethylbenzene | Normal crystallization |
| Hydrolysis | Fuming $H_2SO_4$ | Use 24 equivalent moles of fuming sulfuric acid | Use 12 equivalent moles of fuming sulfuric acid | |
| | $CaCl_2$ drying tube | It was found that when enough sulfuric acid was used, there was no need to use a drying tube since the flask may be closed without the development of significant pressure. | Use a $CaCl_2$ drying tube to protect the fuming sulfuric acid mixture from moisture while allowing bromine and HBr vapor to escape from the solution. This also avoids accumulating vapor pressure inside the flask. | |
| Isolation & purification | | By crystalization & recrystalization | By crystalization & recrystalization | By chromatograph: Silica column, eluent: hexane: ethyl acetate (2:1) |

Now, through his extensive work in synthesizing these compounds, the inventors have discovered an improved method of synthesizing these and other 4-substituted aromatic dialdehyde compounds, which provide increased yields. In one embodiment of the invention, the improved method may involve controlling the amount of fuming sulfuric acid introduced. In another embodiment of the invention, the improved method may involve adding a solid base, such as sodium bicarbonate ($NaHCO_3$), before adding water, and before hydrolysis. The inventors have found that this may significantly increase the yields of final product. The overall procedure is similar to that disclosed above, with a few important differences noted in the following paragraphs.

Let's consider an improved process the inventors have employed to make 4-bromo-OPA from Compound 2. To a round bottom flask, 1 mole equivalent of the brominated compound or product of the bromination reaction, and 12 mole equivalents of fuming sulfuric acid were added. This particular mole ratio of acid to brominated compound is not required. In one embodiment of the invention, a sufficient amount of the sulfuric acid may be added to give a mole ratio of the sulfuric acid to the brominated compound starting material that is from about 10:1 to 14:1. The flask was equipped with a rubber stopper and a $CaCl_2$ drying tube. The mixture was stirred until all bromides are dissolved. Eight mole equivalents of solid sodium bicarbonate ($NaHCO_3$) powder were added or introduced while the mixture was being stirred in an ice bath. The $NaHCO_3$ generally neutralizes the sulfuric acid. The use of this particular amount of the $NaHCO_3$ is not required. In general, the amount should be sufficient to neutralize, or at least reduce, the amount of sulfuric acid. In one embodiment of the invention, a sufficient amount of the sodium bicarbonate may be added or introduced to give a mole ratio of the sodium bicarbonate to the brominated starting compound that is from 5:1 to 11:1. After the mixture stopped bubbling, water was added for the hydrolysis, giving the desired dialdehyde. Accordingly, the introduction of the water, and the hydrolysis, were performed after the introduction of the $NaHCO_3$. This improved process may be expressed as following serial reactions:

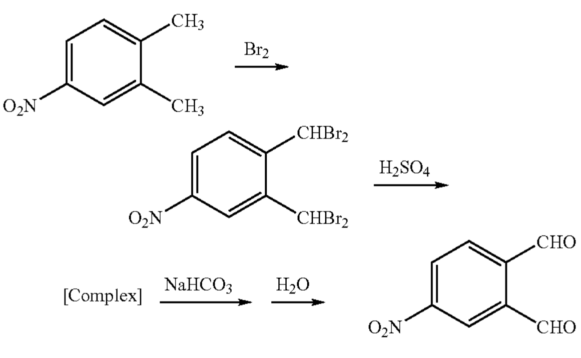

In order to demonstrate the improvements in yield, the inventors have compared the yields resulting from the improved process disclosed above, with the yields obtained by a prior art approach for the synthesis of these compounds. Li et al. (Huaxue Shijie, 26(5), pp. 168-70, 1985) discuss an approach for the preparation of aromatic polyaldehydes, including o-phthalaldehyde, by the hydrolysis of gem-dibromides. As discussed in the abstract, aromatic polyaldehydes $C_6H_{6-n}(CHO)_n$ (n=2, 3) were prepared in good yields by the hydrolysis of corresponding $C_6H_{6-n}(CHBr_2)_n$ with fuming $H_2SO_4$. The dibromides were obtained by the photobromination of $C_6H_{6-n}(CH_3)_n$ in $CCl_4$.

The inventors have used the approach discussed in Li et al. to synthesize o-phthalaldehyde (OPA), and have extended the approach discussed therein in order to synthesize 4-chloro-OPA, 4-bromo-OPA, and 4-nitro-OPA. For convenience, the approach discussed in Li et al. will be referred to herein as the "prior art" synthesis process. The inventors then synthesized o-phthalaldehyde, 4-chloro-OPA, 4-bromo-OPA, and 4-nitro-OPA by the improved synthesis process described above. Table 17 lists the yields obtained for the prior art synthesis process, and the improved synthesis processes enhanced with either controlled acid, or added base.

TABLE 17

| Compounds | Process | Mole equivalent of $H_2SO_4$ to starting material | Mole equivalent of $NaHCO_3$ to starting material | Yield (%) |
|---|---|---|---|---|
| OPA | Prior art(1) | 28.4 | 0 | 79 |
| | Enhanced with controlled acid | 12 | 0 | 86 |
| | Enhanced with added base | 12 | 8 | 91 |
| 4-Chloro-OPA | Prior art(1) | 28.4 | 0 | 66 |
| | Enhanced with controlled acid | 12 | 0 | 88 |
| | Enhanced with added base | 12 | 8 | 88 |
| 4-Bromo-OPA | Prior art(1) | 28.4 | 0 | 17 |
| | Enhanced with controlled acid | 12 | 0 | 88 |
| | Enhanced with added base | 12 | 8 | 92 |
| 4-Nitro-OPA | Prior art(1) | 28.4 | 0 | 2 |
| | Enhanced with controlled acid | 12 | 0 | 28 |
| | Enhanced with added base | 12 | 5.5 | 44 |
| | added base | 12 | 8 | 48 |

As shown, both the enhanced processes give significantly higher yields than the prior art process for each of the compounds. The greatest relative improvements in the yields were observed for 4-bromo-OPA and 4-nitro-OPA.

B. Synthesis of α-Hydroxy Sulfonate Aldehydes

This section shows how to synthesize (2-formyl-phenyl)-hydroxy-methanesulfonic acid, sodium salt, by using o-phthalaldehyde as a starting material. The synthesis proceeds according to the following reaction:

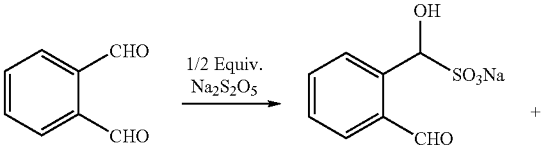

97.9%

-continued

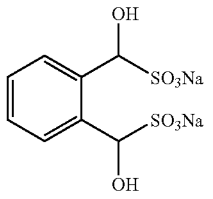

2.1%

In the reaction, the o-phthalaldehyde is reacted in aqueous solution with sodium metabisulfite ($Na_2S_2O_5$) to form the product (2-formyl-phenyl)-hydroxy-methanesulfonic acid, sodium salt. A first solution was prepared by dissolving 5 g (37.3 mmole) phthalaldehyde in 200 mL water. The phthalaldehyde is available from DSM Chemie Linz, located at St. Peter Strasse 25, P.O. Box 296, A-4021 Linz/Austria, among other sources. A second solution was prepared by dissolving 3.54 g (18.64 mmole) sodium metabisulfite in 24.5 g water. The sodium metabisulfate is available from Sigma-Aldrich Co., of Saint Louis, Mo., among other sources. Then, the second solution containing the sodium metabisulfite was added from a dropping funnel gradually to the first solution in a beaker containing the phthalaldehyde with constant stirring at about room temperature. The dropping rate is about 1 drop per eleven seconds. The final solution has a combined volume of about 250 mL. The un-reacted OPA was extracted and removed with 4 times ethyl acetate (3×30mL+1×10 mL) and analyzed with a GC to be about 0.1 g.

C. Other Compounds Commercially Available

Some of the other compounds disclosed herein are commercially available. To further assist those skilled in the art in making and using the compositions disclosed herein, a brief list of vendors are provided, although other vendors may also potentially be available.

Phenyl-propanedial is available from Matrix Scientific, of Columbia, S.C. 4-Pyridinyl-propanedial is available from AKos Building Blocks, Acros Organics, of Loughborough, Leicestershire, United Kingdom, and Matrix Scientific. 2-Pyridinyl-propanedial is available from Acros Organics and Matrix Scientific. 3-(1-Formyl-2-oxoethyl)-2-nitro-benzoic acid is available from Acros Organics and Matrix Scientific. 4-Pyriridinyl-propanedial is available from Acros Organics and Matrix Scientific. 2-Benzoxazolyl-propanedial is available from Acros Organics and Matrix Scientific. (4-Methoxyphenyl)-propanedial is available from Matrix Scientific. [4-(Methylsulfonyl)-2-nitrophenyl]-propanedial is available from Acros Organics and Matrix Scientific. 1,2-Benzenedicarboxaldehyde is available from Alfa Aesar, of Ward Hill, Mass., Fluka, and Sigma-Aldrich, of St. Louis, Mo. 1,3-Benzenedicarboxaldehyde is available from Alfa Aesar, Fluka, and Sigma-Aldrich. 1,4-Benzenedicarboxaldehyde is available from Alfa Aesar, Fluka, and Sigma-Aldrich.

IX. Other Matters

In the description above, for the purposes of explanation, numerous specific details are set forth in order to provide a thorough understanding of the embodiments of the invention. It will be apparent, however, to one skilled in the art that another embodiment may be practiced without some of these specific details. In other instances, well-known structures, devices, and techniques have been shown in block diagram form or without detail in order not to obscure the understanding of this description.

The examples included herein are given as particular embodiments of the invention, to illustrate some of the properties and demonstrate the practical advantages thereof, and to allow one skilled in the art to utilize the invention. It is understood that these examples are to be construed as merely illustrative. For example, the particular concentrations of germicidal compounds are not required. At least to a point, higher concentrations generally provide greater germicidal efficacies, or shorter time to kill, while lower concentrations may be employed with longer times or higher temperatures. Higher concentrations may also be used to ship the compounds to a point of use and then dilution may be used to achieve an appropriate in-use concentration.

Typically, the germicidal compounds will be used in germicidal compositions including the compound as an active ingredient and one or more other ingredients. The one or more other ingredients may include a diluent, an enhancer, a pH-adjusters, buffer salts, chelating agents, corrosion inhibitors, surfactants, coloring agents, and the like. The enhancer may be used to enhance the germicidal efficacy or alter a property of the germicide, such as a staining property. Suitable diluents include, but are not limited to, water, aqueous solutions, alcohols (for example methanol, ethanol, isopropanol, butanol, etc.), polyols (for example ethylene glycol or its oligomers or polymers, propylene glycol or its oligomers or polymers, glycerol, etc.), other organic solvents (for example tetrahydrofuran, dimethylsulfoxide, dimethylformamide, acetone, dioxane, etc.), and combinations of such diluents.

The germicides do not need to be employed at 20° C. (room temperature). Disinfection or sterilization with an aqueous germicidal composition may be carried out at a temperature from about 10° C. to 80° C., or especially from about 20° C. to 60° C. Generally a hotter temperature improves the germicidal efficacy, or shortens the time to kill. As yet another example, the germicidal compositions may be used to kill other than *Mycobacterium terrae* bacteria. The *Mycobacterium terrae* generally are regarded as one of the more difficult bacteria to kill for purposes of disinfection. Less resistant bacteria may be killed in shorter periods of time, or with lesser amounts of the germicidal compounds. Likewise, more resistant microbes, including spores, may be killed in longer periods of time, and with greater amounts of the germicidal compounds.

Many of the methods are described in their most basic form, but operations may be added to or deleted from any of the methods without departing from the basic scope of the invention. It will be apparent to those skilled in the art that many further modifications and adaptations may be made. The particular embodiments are not provided to limit the invention but to illustrate it. The scope of the invention is not to be determined by the specific examples provided above but only by the claims below.

It should also be appreciated that reference throughout this specification to "one embodiment" or "an embodiment" means that a particular feature may be included in the practice of the invention. Similarly, it should be appreciated that in the foregoing description of exemplary embodiments of the invention, various features are sometimes grouped together in a single embodiment, Figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

In the claims, any element that does not explicitly state "means for" performing a specified function, or "step for" performing a specified function, is not to be interpreted as a "means" or "step" clause as specified in 35 U.S.C. Section 112, Paragraph 6. In particular, the use of "step of" in the claims herein is not intended to invoke the provisions of 35 U.S.C. Section 112, Paragraph 6.

While the invention has been described in terms of several embodiments, those skilled in the art will recognize that the invention is not limited to the embodiments described, but may be practiced with modification and alteration within the spirit and scope of the appended claims. The description is thus to be regarded as illustrative instead of limiting.

What is claimed is:

1. A germicidal composition comprising:

a diluent;

an amount of a compound of the following formula effective to kill *mycobacterium*:

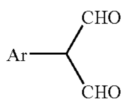

wherein Ar is an aryl group selected from the group consisting of phenyl, 4-pyrimidinyl, and 2-(2-nitro-3-formyl-phenyl); wherein the germicidal composition further comprises an enhancer to enhance a germicidal efficacy of the compound, the enhancer selected from the group consisting of isophthalaldehyde and a combination of isophthalaldehyde and terephthalaldehyde; further wherein the compound has a concentration ranging from 0.1 to about 1%; and a corrosion inhibitor.

2. The composition of claim 1, further comprising:

a buffer;

a chelating agent; and a surfactant.

3. The composition of claim 2, further comprising:

a fragrance; and a coloring agent.

4. The composition of claim 1, wherein Ar is phenyl.

5. The composition of claim 4, wherein the amount of the compound is effective to kill at least $1\times10^6$ *Mycobacterium terrae* bacteria in contact with the composition in less than one hour with a bacteria suspension test at a temperature of 20° C.

6. A germicidal composition comprising:

a diluent;

phenyl-propanedial; and isophthalaldehyde, wherein the germicidal composition is effective to kill *mycobacterium*; further wherein phenyl-propanedial has a concentration ranging from 0.1 to about 1%.

7. The composition of claim 6, wherein the isophthalaldehyde is an enhancer for the germicidal efficacy of the phenyl-propanedial.

8. The composition of claim 6, further comprising terephthalaldehyde.

9. The composition of claim 8, wherein the isophthalaldehyde and the terephthalaldehyde are an enhancer for the germicidal efficacy of the phenyl-propanedial.

10. The composition of claim 1, wherein the amount of the compound is effective to kill at least $1\times10^6$ *Mycobacterium terrae* bacteria in contact with the composition in less than one hour with a bacteria suspension test at a temperature of 20° C.

11. The composition of claim 1, further comprising bacteria in contact with the diluent.

12. The composition of claim 11, wherein the bacteria comprise *mycobacterium.*

13. The composition of claim 12, wherein the bacteria comprise *Mycobacterium terrae.*

14. The composition of claim 1, in contact with a medical instrument.

15. The composition of claim 6, wherein an amount of the phenyl-propanedial is effective to kill at least $1\times10^6$ *Mycobacterium terrae* bacteria in contact with the composition in less than one hour with a bacteria suspension test at a temperature of 20° C.

* * * * *